United States Patent [19]

Bailey

[11] Plant 4,430

[45] Jun. 26, 1979

[54] ROSE PLANT

[75] Inventor: Dorothy J. S. Bailey, Bakersfield, Calif.

[73] Assignee: San Joaquin Rose Company, McFarland, Calif.

[21] Appl. No.: 903,381

[22] Filed: May 5, 1978

[51] Int. Cl.[2] ..... A01H 5/00

[52] U.S. Cl. ..... Plt./12

[58] Field of Search ..... Plt./12

*Primary Examiner*—Robert E. Bagwill
*Attorney, Agent, or Firm*—Vincent G. Gioia

[57] ABSTRACT

A novel rose variety of the hybrid tea class characterized by flowers of unique red and yellow coloring, high-center blooms, usually borne singly on a vigorous upright growing plant as shown and described.

1 Drawing Figure

1

The present invention relates to a new and distinct variety of rose plant of the hybrid tea class, which was originated by my crossing the rose variety known as "Grand Gala" (U.S. Plant Pat. No. 1,489) as seed parent with the rose variety known as "Peace" (U.S. Plant Pat. No. 591) as pollen parent.

Among the novel characteristics possessed by this new variety which distinguish it from its parents and all other varieties of which I am aware are: (1) flowers of unusual red and yellow bicolor with red coloring on the upper petal surface and yellow coloring on the reverse displaying a bright vermillion tonality as the blooms age and the underside of the petals become obscured, (2) flowers of high center form which are very long lasting on the plant and have a medium damask fragrance (3) abundant foliage of leathery texture, and (4) few thorns. Asexual reproduction by budding of the new variety as performed in Kern County, Calif., shows that the foregoing and other distinguishing characteristics come true to form and are established and transmitted through succeeding propagations.

A main distinguishing feature of the new and improved rose variety is its unusual red and yellow bicoloring of the flowers which are produced in good size and in large quantities. With petals of different upper and under surface colors, flowers present an ever changing color display and general tonality.

Flowers of this new variety are usually borne singly, opening from large ovoid buds and maintaining the high center effect as it ages. The red and yellow colored petals are velvety inside and satiny outside and have good substance making them long lasting on the plant and after cutting. The abundant, thick, leathery foliage provides a fine background for the unusual distinctive and attractive bicolor blooms which result in a deep vermillion display of aging bloom concealing the yellow coloring except at the "eye" of the flower.

The accompanying drawing shows typical specimens of the flowers and vegetative growth of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "13C" is plate 13C of the Royal Horticultural Society Color Chart.

2

Parentage: Seedling.
*Seed parent.*—"Grand Gala".
*Pollen parent.*—"Peace".
Class: Hybrid tea.

The following observations are made of specimens grown outdoors at Kern County, Calif., during the month of June.

1. FLOWER

Blooming habit: Continuous.

A. Bud:
- (1) *Size.*—Large.
- (2) *Form.*—Ovoid.
- (3) *Color.*—When sepals first divide: near 13C with 46A veining on outer petals. When petals begin to unfurl: 12C with 46A on inner petal surface. When half-blown: inside of petals — 46C; reverse side of petals — 12C at base washing to ivory 11C.
- (4) *Sepals.*—Thick, pointed, about ¾ length of bud. Color: dull, light green.
- (5) *Peduncle.*—Length — 3½ to 4 inches. Aspect — smooth. Strength — thick, erect. Color — 182A.

B. Bloom:
- (1) *Size.*—Average size when fully expanded 4½ to 5½ inches.
- (2) *Borne.*—Usually singly.
- (3) *Form.*—High centered, holds well as flower opens; open flower retains high center effect.
- (4) *Petalage.*—Number of petals under normal conditions — about 30–32.
- (5) *Color.*—Center of flower — 46A. Outer petals — 46C. Reverse of petals — 12C washing to ivory 11C. Base of petals — 12C. General tonality from a distance — bright yellow and red blend.
- (6) *Color change.*—As bloom ages — bright vermillion when under surface of petals (yellow) are less visible upon opening. General tonality — 46B with light yellow swirl at center of bloom. After three or more days — 46C.

C. Petals:
- (1) *Texture.*—Very thick.
- (2) *Appearance.*—Inside — velvety; outside — satiny.
- (3) *Form.*—Ovoid, large.

(4) *Arrangement.*—Regularly arranged, shingle-like.

(5) *Petaloids in center.*—Few.

(6) *Persistence.*—Drop off clean.

(7) *Fragrance.*—Medium damask.

(8) *Lasting quality.*—Very long lasting on the plant and as a cut flower.

2. REPRODUCTIVE ORGANS

A. Stamens, anthers:

(1) *Arrangement.*—Several rows arranged around styles.

(2) *Color.*—20B.

B. Pollen: Color — 16C.

C. Styles: Bunches; short, thick.

D. Stigmas: Color — 58D.

E. Hips:

*Shape.*—Globular.

*Color.*—169D when mature, seeds do not protrude.

3. PLANT

A. Form: Upright.

B. Growth: Very vigorous, upright.

*Height attained.*—3½ to 4½ ft. during normal growing season.

C. Foliage: Compound of 5 to 7 leaves.

(1) *Size.*—Large.

(2) *Quantity.*—Abundant.

(3) *Color.*—New foliage: upper side — 146A; under side — 138B. Old foliage: upper side — 137A; under side — 138B with reddish cast.

(4) *Shape.*—Pointed.

(5) *Texture.*—Upper side — thick, smooth, very waxed. Under side — leathery, rough with veining.

(6) *Edge.*—Serrated.

(7) *Serration.*—Small and uniform.

(8) *Leaf stem.*—Color — 137C; under side — 137B with 182A.

(9) *Stipules.*—Slightly bearded.

D. Wood:

(1) *New wood.*—Color — 182A. Bark — smooth.

(2) *Old wood.*—Color — 137D colored with 182A on surface exposed to weather. Bark — smooth.

E. Thorns:

(1) *Thorns.*—Quantity: on main stalks from base — very few; on laterals from stalk — none. Form: flat. Length: medium. Color when young — 182B. Position — irregular.

(2) *Prickles.*—Quantity: on main stalks — none; on laterals — none.

F. Plant's disease resistance:

*Mildew.*—Very good.

*Blackspot.*—Good.

*Rust.*—None observed.

G. Winter hardiness: Hardy.

I claim:

1. A new and distinct variety of rose plant of the hybrid tea class, substantially as shown and described, characterized particularly by flowers of unique red and yellow coloring resulting from petals with upper red velvety surface and yellow satiny reverse displaying a variable general tonality upon opening, high-center blooms holding form well upon aging and thick petals such that the blooms last well on the plant and as a cut flower, borne usually singly on a vigorous upright, growing plant with abundant, strong foliage.

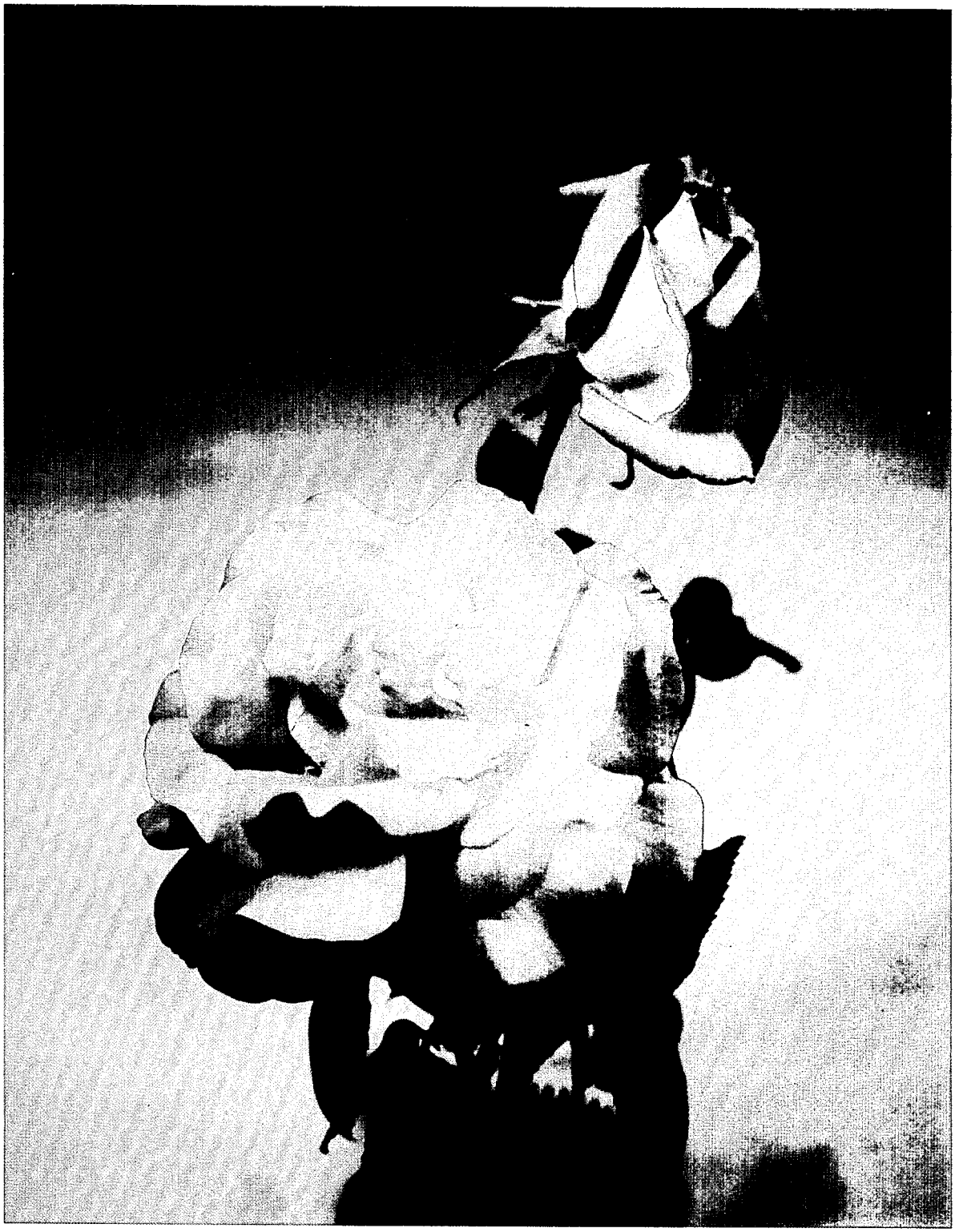

* * * * *